United States Patent
Hofmann

(10) Patent No.: US 9,476,848 B1
(45) Date of Patent: Oct. 25, 2016

(54) NMR FLOW CELL

(71) Applicant: Bruker BioSpin GmbH, Rheinstetten (DE)

(72) Inventor: Martin Hofmann, Bad Herrenalb (DE)

(73) Assignee: Bruker BioSpin GmbH, Rheinstetten (DE)

( * ) Notice: Subject to any disclaimer, the term of this patent is extended or adjusted under 35 U.S.C. 154(b) by 0 days.

(21) Appl. No.: 15/071,331

(22) Filed: Mar. 16, 2016

(30) Foreign Application Priority Data

Apr. 2, 2015 (DE) .................. 10 2015 206 030

(51) Int. Cl.
  *G01N 24/08* (2006.01)
  *G01R 33/31* (2006.01)
  *G01R 33/30* (2006.01)
  *G01R 33/46* (2006.01)

(52) U.S. Cl.
  CPC ............. *G01N 24/08* (2013.01); *G01R 33/307* (2013.01); *G01R 33/31* (2013.01); *G01R 33/46* (2013.01)

(58) Field of Classification Search
  CPC .... G01R 33/307; G01R 33/30; G01R 33/31; G01R 33/46; G01N 24/08
  USPC ....... 324/300, 306, 307, 309, 315, 318, 321, 324/322
  See application file for complete search history.

(56) References Cited

U.S. PATENT DOCUMENTS

| 8,686,729 B2 | 4/2014 | Marquez | |
| 2002/0155625 A1* | 10/2002 | Chapman | G01N 22/00 436/536 |
| 2007/0257676 A1* | 11/2007 | Sacher | G01R 33/34015 324/318 |
| 2009/0121712 A1* | 5/2009 | Han | G01R 33/282 324/307 |
| 2010/0321018 A1* | 12/2010 | Takegoshi | G01R 33/3403 324/318 |

* cited by examiner

*Primary Examiner* — Dixomara Vargas
*Assistant Examiner* — Rishi Patel
(74) *Attorney, Agent, or Firm* — Paul Vincent

(57) ABSTRACT

Monitoring cell (100) for performing an NMR measurement of a reaction fluid. The monitoring cell (100) has a hollow NMR sample probe (110) for receiving the reaction fluid. Inlet and outlet transport capillaries (112, 123) transport the reaction fluid to and from the sample probe (110). A feed line (306) and return line transport a temperature control fluid to and from the monitoring cell (100). An adapter head (108) couples the transport capillaries (112, 123) to the sample probe (110) and removably connects the sample probe (110) to an adapter section (106). The transport capillaries (112, 123) are positioned within the feed line (306) in parallel to one another. The feed and the return lines (306, 358) are attached to the adapter section (106) such that a reversal of the temperature control fluid stream occurs in the adapter section (106).

18 Claims, 2 Drawing Sheets

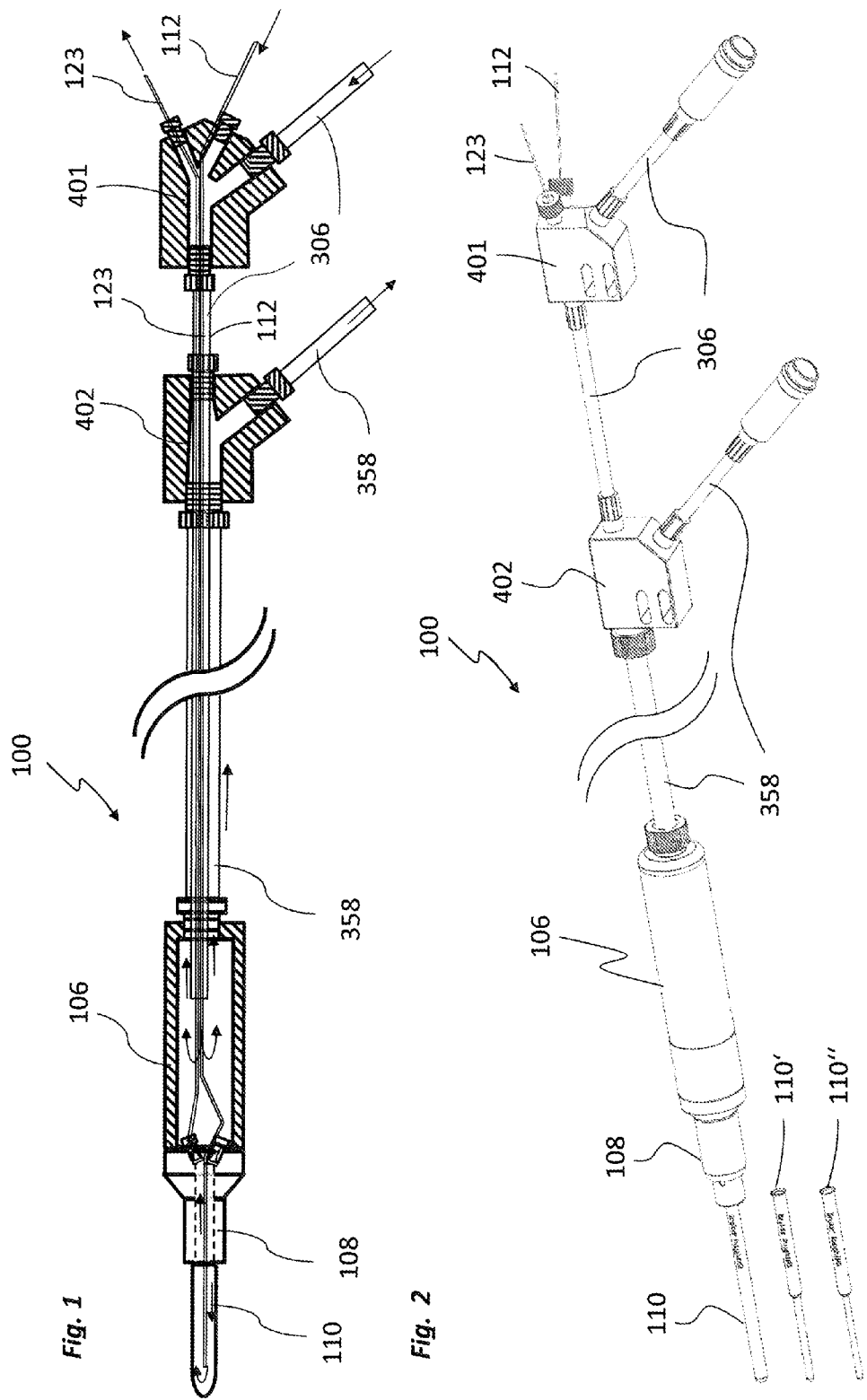

NMR FLOW CELL

This application claims Paris convention priority from DE 10 2015 206 030.6 filed Apr. 2, 2015 the entire disclosure of which is hereby incorporated by reference.

BACKGROUND OF THE INVENTION

The invention relates to a monitoring cell for performing a measurement in an NMR spectrometer of a reaction fluid produced in a reaction vessel, in particular for monitoring a chemical reaction by means of NMR spectroscopy, wherein the monitoring cell has the following components: a hollow sample probe for receiving the reaction fluid to be measured in the NMR spectrometer; an inlet transport capillary for receiving the reaction fluid from the reaction vessel and for transporting the reaction fluid from the reaction vessel to the sample probe; an outlet transport capillary for return transport of the reaction vessel from the sample probe to the reaction vessel; a device for conducting the temperature control fluid around the inlet and outlet transport capillaries, which comprises a feed line for delivering the temperature control fluid to the monitoring cell, and a return line for return of the temperature control fluid from the monitoring cell, the feed line being coaxially positioned within the return line; an adapter section through which the transport capillaries are fed; and an adapter head at the probe end of the adapter section, which is designed for coupling of the transport capillaries to the sample probe, the inlet capillary projecting into the sample probe and the adapter head separably connecting the sample probe to the adapter section. Such a monitoring cell, configured as an NMR flow cell, is known from U.S. Pat. No. 8,686,729 B2 or the parallel EP 2 407 796 B1.

The present invention relates generally to the field of continuous monitoring of chemical reactions by means of NMR spectroscopy.

NMR spectroscopy is a widespread measurement method by which chemical compounds can be analyzed. Usually in NMR spectroscopy, a sample to be measured in a sample tube is given in a sample probe, which is measured in an NMR spectrometer.

Chemical reaction monitoring essentially involves optimization of reaction parameters (temperature, pressure, solvent, catalyst . . . ) with the purpose of displacing the reaction equilibrium toward the product side and/or suppressing a faulty reaction. Thus, in order to maintain permanent reaction monitoring by means of NMR spectroscopy, samples must be taken regularly, which would constitute a great expense.

During the sample transfer, the reaction conditions (for example, the temperature and pressure) should be maintained so that the sample that is to be measured does not change. The time factor plays a significant role in this process.

Since the NMR spectrometer and the chemical reactor are spatially separated and the reaction monitoring is carried out in a closed system, the reaction mixture is pumped continuously from the reactor into the sample probe, where it is measured at regular intervals. The conditions in the transport system must be as close as possible to those predominating in the reaction vessel. This applies in particular to the reaction temperature.

In the initially cited U.S. Pat. No. 8,686,729 B2 or the parallel EP 2 407 796 B1, in each case a flow cell for chemical reaction monitoring by means of NMR spectroscopy is described. With the known device, the liquid reaction mixture is pumped continuously from the reactor to the NMR sample probe in the measurement device, where the liquid reaction mixture is measured.

The known system functions with a total of four coaxial tubes positioned within one another, the two inner capillaries comprising the transport capillaries for the reaction mixture. The two outer tubes are for circulating a temperature control fluid. The system consists basically of the following four parts:

1. Housing for reversal of the temperature control lines
2. Coupler section for decoupling of the transport capillaries from the temperature control lines
3. Ceramic head for separation of the transport capillaries into feed and return and
4. Sample probe (measurement cell), which contains only a feeder capillary of the reaction mixture.

In order to connect the four coaxial lines comprising the feed or return lines, several connecting sites are necessary, which results in great complexity of the system, as shown in the present FIG. 3 (taken from EP 2 407796 B1).

In addition, a coupling piece (see item 2 above) is provided in the known device, which decouples the capillaries of the reaction stream from the temperature control lines in order to feed the capillaries to the measurement cell. This creates a relatively large area in which the reaction mixture is not temperature-controlled, but exposed to room temperature. This is in particular a problem when working with thin capillaries and when the reaction temperature differs greatly from the room temperature. In this constellation, an exothermic chemical reaction can slow or alter the thermal equilibrium. For reactions that proceed at temperatures below 0° C., this can lead to an uncontrollable alteration of the sample condition at this exposed site.

It must therefore be ensured that the through flow in the heating or cooling circuit can be operated with commercially available circulation thermostats and the temperatures necessary for the reaction can be maintained over the entire length without significant loss. This means that resistors (such as T-connectors, for example) in the temperature control lines considerably reduce the flow, and thus cannot guarantee a temperature that remains the same within narrow limits over the entire length of the sample feed.

Furthermore, due to the known design, the volume of the return sample capillary is many times greater than that of the sample feed capillary, namely by a factor of around 5. Because of this, the circulation period until the sample to be measured is again transported back to the reactor is relatively long, which once again can negatively affect the reaction in the reactor.

Replacement of the sample probe (NMR flow tube) can only be carried out with a special tool. The connection must be irreversibly destroyed in the process (snap-cap, cut with a razor blade).

As mentioned, the temperature is an essential factor which greatly influences the reaction speed of chemical reactions. Herein lies the great difficulty of maintaining chemical equilibrium especially as regards the temperature. Further, the system for sampling must be structured as simply as possible, that is, it should be configured with as few connections and attachment sites as possible. Such sites are the ones that are frequently identified as weak links in the transport of fluids, where leaks can occur.

The invention is based on the relatively demanding and complex task of maintaining as uniform a temperature as possible in a monitoring cell of the above described type with inexpensive technical means in the feeder and return lines of the fluid measurement sample, in order not to influence the thermal equilibrium, and of simply designing the sampling system in such a way that as few as possible, as standardized as possible connection or attachment sites can be used, easily obtainable in commerce, while already existing devices must be easily upgradeable.

SUMMARY OF THE INVENTION

This task is achieved by the present invention in a both surprisingly simple and effective manner in that the transport capillaries are positioned within the feed line parallel to one another—not coaxially—and both transport capillaries are attached in a fluid-tight manner to the adaptor head; and that the feeder and return line for the temperature control fluid are configured and attached to the adapter section in such a way that a reversal of the temperature control fluid stream occurs in the adapter section.

In comparison with the coaxial design with four lines laid inside of one another, in the present invention the transport capillaries for the reaction mixtures are positioned separately. The two transport capillaries for feeding and returning the reaction fluid from the reaction vessel to the sample probe and back to the reactor are surrounded by a temperature control fluid (as a rule a liquid), if possible, over the entire length of the sample probe, which makes it possible to keep the reaction mixture at the desired temperature.

The temperature control fluid is carried in coaxial lines, wherein the inner line is the feeder and the outer line is the return line of the temperature control fluid to a common vessel.

The transport capillaries for the reaction mixture are inserted into the feed line in direct proximity to the reaction vessel by means of a preferably Y-shaped attachment piece. In a further, likewise preferred Y-shaped attachment piece, the feeder along with the transport capillaries is inserted in the return. Using this design, the reaction mixture can be transported over several meters to the NMR spectrometer with the temperature remaining the same.

Directly in front of the sample probe, the temperature control stream is reversed in an adapter section, with the two temperature control lines communicating via the volume of the adapter piece.

The adapter piece terminates on the spectrometer side with a locking head (adapter head), through which only the transport capillaries, but not the temperature control stream, are fed.

The sample probe, into which the inlet transport capillary preferably immerses more deeply than the outlet transport capillary, is attached to the adapter head. The outlet transport capillary preferably terminates at the adapter head.

The reaction mixture flows from the inlet capillary into the sample probe; the probe is thus filled to the full measurement volume and is permanently flushed by the reaction mixture.

The reaction mixture is transported back into the reactor through the opening of the outlet capillary.

In particular, the following advantages are achieved with the present invention:

An improved temperature control over the entire range all the way to the measurement probe is possible.
The coupling section from the prior art is omitted.
Fewer fittings result in fewer weak spots, which in turn results in fewer leakages in the system and in a simpler design.
The only region which is not temperature-controlled is the adapter head, but it is partially temperature-controlled by the gas stream of the NMR spectrometer on the side of the sample probe.
Volume control for the sample return is enabled.
More economical fabrication is achieved by means of a markedly smaller number of necessary components and by using commercially available dimensions.
Easier adjustment to the application is achieved.

Especially simple and therefore preferred is an embodiment of the inventive monitoring cell in which the feeder and the return lines communicate with one another via a hollow volume of the adapter section in such a way that the temperature control medium stream is reversed in the adapter section.

In a further advantageous embodiment of the invention, the inlet transport capillary immerses more deeply into the sample probe than the outlet transport capillary, in particular the outlet transport capillary terminates with a locking head (the adapter head), through which only the transport capillaries but not the temperature control stream are conducted. The outlet transport capillary then does not enter the sample probe. The reaction mixture flows out of the inlet capillary into the sample probe and the probe is thus filled to the full measurement volume and permanently flushed by the reaction mixture. The reaction mixture is transported back into the reactor through the opening of the outlet capillary.

Preferably both the adapter section and the adapter head are designed with heat insulation on the outside. The adapter piece on the sample probe side is thus insulated against temperature loss, just as the entire temperature control fluid feed.

The preferred class of embodiments of the invention includes the adapter head made from polytetrafluoroethylene (=Teflon®), preferably with fiberglass reinforcement. This material is more rugged and less porous than the ceramic according to the prior art, which is advantageous for cleaning and reuse and inertness with respect to chemical substances. In addition, this material allows boreholes to be made into which standard fixtures of the transport capillaries can be screwed in a fluid-tight manner.

The system can be used in temperatures from −40° C. to +120° C., preferably from −10° C. to +60° C.

A further advantageous embodiment of the inventive monitoring cell is provided in that between the sample probe and the adapter head there is a quick-release connector that is manually detachable, preferably without tools, in particular a reusable bayonet connector, for simple and rapid replacement of the sample probe when it becomes dirty, when there is an application change, or a change in volume of the measurement range.

In preferred embodiments, the transport capillaries have identical outer dimensions. The use of two identically dimensioned capillaries in terms of their outer dimensions for the sample circuit makes it possible, inter alia, to provide better volume control for the returning sample capillary. It can now be freely selected with respect to the internal volume, and in the most favorable case can be identical to that of the capillary returning the samples.

Through selection of the commercially available dimensions for capillaries and fittings, the product can be manufactured about 50% more economically and can be adapted even more easily to the requirements of the reaction (internal volume).

In further advantageous embodiments of the inventive monitoring cell, the transport capillaries are made from chemically inert plastic, preferably PTFE. Commercially available chemically inert PTFE capillaries are used, which allow the use of commercially available fittings and do not require the special manufacture of tube connections.

The outlet transport capillary preferably has a larger inner diameter—in particular, twice the size if needed—than the inlet capillary. This is advantageous for the removal of precipitates that may form in the sample probe.

The inner diameter of the transport capillaries, depending on the requirements of the reaction, is between 0.1 and 1.2 mm. Especially favorably, the inner diameter is from 0.25 to 0.5 mm. The feed and return capillary preferably have a 0.5 mm inner diameter in order to keep the pressure drop arising along the length of 4 m to 6 m as low as possible, with simultaneous allowance for the internal system volume. The pressure drop for a pump delivery rate of 5 mL/min at room temperature with water is then around 1 bar/m (capillary).

Also advantageous are embodiments of the inventive monitoring cell in which the feed and the return line of the temperature control fluid over a distance of from 3 m to 6 m have an inner diameter between 2 mm and 10 mm, preferably around 3.5 mm for the feeder and 7 mm for the return.

In further preferred embodiments of the invention, a first Y-shaped coupling piece is provided, with which the transport capillaries can be inserted in the device for conducting the temperature control fluid.

Further, a second Y-shaped coupling can be provided, with which the feed and the return line can be inserted in the device for conducting the temperature control fluid.

In particularly advantageous embodiments, an inlet and an outlet of the Y-shaped coupling pieces enclose an angle of around 45©, so that, when commercially available circulation thermostats are used, the volume stream of the temperature control fluid can also be increased by around 40% with respect to the T-shaped coupling pieces at a 90° angle.

Quite particularly preferred are variants of the invention in which the temperature control fluid is a liquid. Temperature control with a temperature control gas would be much less effective, as gas is not a good heat carrier.

The scope of the present invention also includes the use of the system with the above described inventive qualities for reaction control of a chemical reaction by means of NMR spectroscopy.

Further advantages of the invention arise from the description and the drawing. The above-named and further cited features can also be used individually for themselves or severally in any combination. The shown and described exemplary embodiments should not be understood as an exhaustive list, but rather are exemplary in nature for describing the invention.

The invention is represented in the drawing and is explained more closely with reference to the exemplary embodiments, wherein:

BRIEF DESCRIPTION OF THE DRAWING

FIG. 1 is a schematic vertical section view of an embodiment of an inventive monitoring cell;

FIG. 2 is a schematic three-dimensional view of this embodiment from the side.

DESCRIPTION OF THE PREFERRED EMBODIMENT

Figure 3:
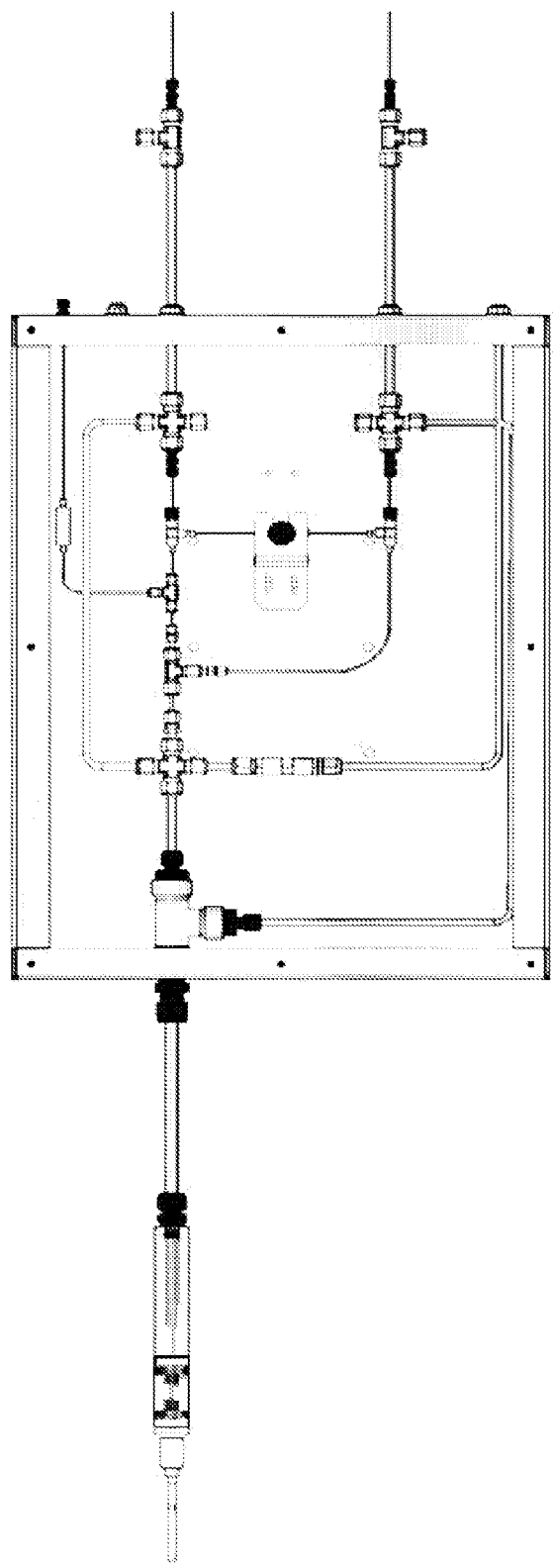
FIG. 3 is a representation of a monitoring cell in accordance with the prior art.

FIGS. 1 and 2 of the drawing show in a schematic view of a preferred embodiment of the inventive monitoring cell 100. This serves to perform a measurement of a reaction fluid produced in a reaction vessel in an NMR spectrometer, in particular for monitoring a chemical reaction by means of NMR spectroscopy. This is therefore a flow cell for chemical reaction monitoring by means of NMR. With the inventive device, the reaction mixture is continuously pumped from the reactor to the NMR sample probe in the measurement unit, where it is measured. In this process it is always very difficult to maintain the chemical equilibrium, in particular with respect to temperature.

The monitoring cell 100 has the following components:
a hollow NMR sample probe 110 for receiving the reaction fluid to be measured in the NMR spectrometer;
an inlet transport capillary 112 for receiving the reaction fluid from the reaction vessel and for transport of the reaction fluid from the reaction vessel to the sample probe 110;
an outlet transport capillary 123 for return transport of the reaction fluid from the sample probe 110 to the reaction vessel;
a device for conducting the temperature control fluid around the inlet and outlet transport capillaries 112 and 123, which comprises a feed line 306 for feeding the temperature control fluid to the monitoring cell 100 and a return line 358 for return of the temperature control fluid from the monitoring cell 100, the feed line 306 being coaxially positioned within the return line 358;
an adapter section 106, through which the transport capillaries 112 and 123 are conducted; and
an adapter head 108 on the sample side end of the adapter section 106, which is configured for coupling of the transport capillaries 112 and 123 to the sample probe, wherein the inlet transport capillary 112 extends into the sample probe 110, and wherein the adapter head 108 detachably connects the sample probe 110 to the adapter section 106.

The inventive monitoring cell 100 is characterized in that the transport capillaries 112 and 123 are positioned within the feed line 306 in parallel to one another—not coaxially—and both transport capillaries 112 and 123 are attached in a fluid-tight manner to the adapter head 108;

and that the feed and the return lines 306 and 358 are configured for the temperature control fluid and attached to the adapter section 106 in such a way that a reversal of the temperature control fluid stream occurs in the adapter section 106.

Fixation of the sample probe 110 with a reusable bayonet connector (not shown in the drawing) allows rapid and simple replacement.

The volume stream of the temperature control fluid is improved primarily by two measures:
Reduction of the number of (relevant) tube connections from the previous 28 to 12.
Instead of the seven T-connectors with 90° angles, now two Y-connectors 401 and 402 with 45° angles are used, which increased the volume flow of the temperature control fluid when commercially available circulation thermostats are used by around 40%.

Use of two identically dimensioned capillaries 112 and 123 in terms of outer dimensions for the sample circuit also allows better volume control for the returning sample capillary 123. It can now be freely selected with respect to the internal volume and in the most favorable case can be identical to the capillary 112 feeding the samples.

By selection of commercially available dimensions for capillaries and connections, the product can be manufactured around 50% more economically and at the same time can be even more easily adapted to the requirements of the reaction (internal volume).

The adapter head 108 is usually made of fiberglass reinforced Teflon®. This material is more rugged and less porous than the ceramic as provided in the prior art, which is advantageous for cleaning and reuse as well as for inertness with respect to chemical substances. In addition, this material allows boreholes and threads to be made, into which standard connections of the transport capillaries can be screwed in a fluid-tight manner.

The system can be used at temperatures from −40° C. to +120° C., in particular from −10° C. to +60° C.

Preferably the outlet transport capillary 123 has a larger inner diameter than the inlet transport capillary 112, preferably the same or as needed a maximum of two times larger. This is advantageous for the removal of possible precipitates in the sample probe 110. The inner diameter of the transport capillaries is from 0.1 to 1.2 mm, especially preferably the inner diameter is from 0.25 to 0.5 mm. Preferably the pressure drop for a pump delivery rate of 5 mL/min at room temperature with water is then around 1 bar/m (capillary).

The system according to the invention further comprises a first Y-shaped coupling piece 401, with which the transport capillaries 112, 123 are inserted into the temperature control fluid feed line 306.

The described system preferably comprises a second Y-shaped coupling 402, with which the temperature control fluid feed line 306 is coupled to the temperature control fluid return line 358.

Commercially available chemically inert PTFE capillaries are used, which allow the use of commercially available connectors. Special fabrication of tube attachments is thus no longer necessary.

The sample probe side of the adapter piece 106 is formed such that, just as the entire temperature control fluid feed and the entire NMR flow cell, it can be insulated against temperature loss.

In addition, the sample probe 110 can be secured with a quick-release connector that can be released manually and without special tools for simple changing of the sample probe when it becomes dirty, when there is an application change or a volume change of the measurement range.

The invention allows the insertion of several sample probes 110, 110', 110" differing in their measurement volume, as shown in FIG. 2, in order to give the user the option of specific adjustment to the application and a thereby resulting sample concentration. The active volume in the measurement range can be 460 μL; 130 μL; or 90 μL, for example.

Finally, FIG. 3 shows the NMR flow cell known from the prior art, as discussed above in detail.

I claim:

1. A monitoring cell for performing a measurement in an NMR spectrometer of a reaction fluid produced in a reaction vessel, the monitoring cell comprising:
a hollow NMR sample probe for receiving the reaction fluid to be measured in the NMR spectrometer;
an inlet transport capillary for receiving the reaction fluid from the reaction vessel and for transport of the reaction fluid from the reaction vessel to said sample probe;
an outlet transport capillary for return transport of the reaction fluid from said sample probe to the reaction vessel;
a device for conducting a temperature control fluid around said inlet and outlet transport capillaries, said device comprising a feed line for feeding the temperature control fluid to the monitoring cell and a return line for return of the temperature control fluid from the monitoring cell, said feed line being coaxially positioned within said return line;
an adapter section, through which said inlet and outlet transport capillaries are fed; and
an adapter head disposed on a sample-side end of said adapter section, said adapter head being configured for coupling said inlet and outlet transport capillaries to said sample probe, wherein said inlet transport capillary extends into said sample probe and said adapter head connects said sample probe to said adapter section in a detachable manner, said net and outlet transport capillaries thereby being positioned within said feed line in parallel to one another and not coaxially and each of said inlet and outlet transport capillaries is attached to said adapter head in a fluid-tight manner, wherein said feed and said return lines are configured for the temperature control fluid and attached to said adapter section in such a way that a reversal of a temperature control fluid stream occurs in said adapter section.

2. The monitoring cell of claim 1, wherein said feed line and said return line communicate with one another via a hollow volume of said adapter section in such a way that the temperature control fluid stream is reversed in said adapter section.

3. The monitoring cell of claim 1, wherein said inlet transport capillary immerses more deeply in said sample probe than said outlet transport capillary.

4. The monitoring cell of claim 3, wherein said outlet transport capillary terminates at said adapter head and does not immerse in said sample probe.

5. The monitoring cell of claim 1, wherein said adapter section and said adapter head comprise a heat insulation towards an outside.

6. The monitoring cell of claim 1, wherein said adapter head is made from polytetrafluoroethylene.

7. The monitoring cell of claim 6, wherein said polytetrafluoroethylene is fiberglass reinforced.

8. The monitoring cell of claim 1, further comprising a quick release or bayonet connector that can be detached manually or without tools and which is disposed between said sample probe and said adapter head.

9. The monitoring cell of claim 1, wherein said inlet and outlet transport capillaries have identical outer dimensions.

10. The monitoring cell of claim 1, wherein said inlet and outlet transport capillaries are made from chemically inert plastic or from PTFE.

11. The monitoring cell of claim 1, wherein said outlet transport capillary has a larger inner diameter than that of said inlet transport capillary.

12. The monitoring cell of claim 11, wherein said outlet transport cavity has an inner diameter which is twice as large as that of said inlet transport capillary.

13. The monitoring cell of claim 1, wherein said inlet and outlet transport capillaries have inner diameters between 0.1 mm and 1.2 mm or between 0.2 and 0.5 mm.

14. The monitoring cell of claim 1, wherein, over a distance of 3 m to 6 m, said feed line and said return line have an inner diameter between 2 mm and 10 mm, of about 3.5 mm for said feed line or of about 7 mm for said return line.

15. The monitoring cell of claim 1, further comprising a first Y-shaped coupling piece with which said inlet and outlet transport capillaries can be inserted into said device for conducting the temperature control fluid.

16. The monitoring cell of claim 15, further comprising a second Y-shaped coupling piece with which said feed line and said return line can be inserted in said device for conducting the temperature control fluid.

17. The monitoring cell of claim 16, wherein an inlet and an outlet said first and said second of Y-shaped coupling pieces enclose an angle of about 45°.

18. The monitoring cell of claim 1, wherein the temperature control fluid is a liquid.

* * * * *